United States Patent
Soni et al.

(10) Patent No.: US 10,813,916 B2
(45) Date of Patent: Oct. 27, 2020

(54) IMMEDIATE RELEASE PHARMACEUTICAL COMPOSITION OF TIZANIDINE

(71) Applicant: Jubilant Generics Limited, Noida, Uttar Pradesh (IN)

(72) Inventors: Pankaj Soni, Sirsa (IN); Rashmi Ranjan Panda, Noida (IN); Ganesh Vinayak Gat, Pune (IN); Dinesh Kumar, Chandigarh (IN); Kamal S. Mehta, Noida (IN); Ravikumar Nithiyanandam, Coimbatore (IN)

(73) Assignee: Jubilant Generics Limited (IN)

( * ) Notice: Subject to any disclaimer, the term of this patent is extended or adjusted under 35 U.S.C. 154(b) by 296 days.

(21) Appl. No.: 15/577,141

(22) PCT Filed: May 27, 2016

(86) PCT No.: PCT/IB2016/053124
§ 371 (c)(1),
(2) Date: Nov. 27, 2017

(87) PCT Pub. No.: WO2016/193880
PCT Pub. Date: Dec. 8, 2016

(65) Prior Publication Data
US 2018/0207139 A1    Jul. 26, 2018

(30) Foreign Application Priority Data
May 29, 2015    (IN) .......................... 1547/DEL/2015

(51) Int. Cl.
*A61K 31/433*    (2006.01)
*A61K 9/16*    (2006.01)
*A61K 9/48*    (2006.01)

(52) U.S. Cl.
CPC .......... *A61K 31/433* (2013.01); *A61K 9/1635* (2013.01); *A61K 9/4866* (2013.01)

(58) Field of Classification Search
CPC ... A61K 31/433; A61K 9/1635; A61K 9/4866
See application file for complete search history.

(56) References Cited

U.S. PATENT DOCUMENTS

| | | | | |
|---|---|---|---|---|
| 2004/0220240 | A1* | 11/2004 | Pellegrini | A61K 9/1676 514/363 |
| 2007/0148211 | A1* | 6/2007 | Altreuter | A61K 9/0056 424/441 |
| 2008/0194655 | A1* | 8/2008 | Bull | A61K 9/0004 514/362 |
| 2008/0279819 | A1* | 11/2008 | Went | A61K 31/13 424/85.6 |
| 2009/0156683 | A1* | 6/2009 | Simmons | A61K 9/0095 514/618 |
| 2010/0166856 | A1* | 7/2010 | Garcia-Salgado Lopez | A61K 31/5415 424/459 |
| 2010/0221333 | A1* | 9/2010 | Schlutermann | A61K 9/0056 424/465 |

FOREIGN PATENT DOCUMENTS

WO    WO 2016046189 A1 *    1/2016

OTHER PUBLICATIONS

Khan et al., Formulation of Two-Drug Controlled Release Nonbiodegradable Microparticles for Potential Treatment of Muscles Pain and Spasm and Their Simultaneous Spectrophotometric Estimation. Acta Poloniae Pharmaceutica ñ Drug Research, vol. 67 No. 3 pp. 299-306, 2010 (Year: 2010).*

Masareddy et al., Development of Orodispersible Tizanidine HCl Tablets Using Spray Dried Coprocessed Exipient Bases, Indian J Pharm Sci. Jul.-Aug. 2011; 73(4): 392-396. (Year: 2011).*

Zade et al., Formulation, Evaluation and Optimization of Fast dissolving tablet containing Tizanidine Hydrochloride, International Journal of PharmTech Research, vol. 1, No. 1, pp. 34-42, Jan.-Mar. 2009. (Year: 2009).*

* cited by examiner

*Primary Examiner* — Lakshmi S Channavajjala
(74) *Attorney, Agent, or Firm* — William D. Hare, Esq.; McNeely, Hare & War, LLP

(57) ABSTRACT

The present invention relates to an immediate release solid oral pharmaceutical composition comprising an effective amount of Tizanidine or its pharmaceutically acceptable salts, esters, solvates, polymorphs, stereoisomers or mixtures thereof. The solid oral dosage form comprises one or more methacrylic acid copolymers or its derivatives and is bioequivalent to the commercially available counterpart (ZANAFLEX® capsule) after oral administration. The invention also relates to a process for preparation of a pharmaceutical capsule dosage form comprising an effective amount of Tizanidine Hydrochloride wherein, the dosage form comprises methacrylic acid copolymer or its derivatives.

20 Claims, No Drawings

IMMEDIATE RELEASE PHARMACEUTICAL COMPOSITION OF TIZANIDINE

FIELD OF THE INVENTION

Present invention in general relates to a stable pharmaceutical composition comprising Tizanidine or its pharmaceutically acceptable salts, esters, solvates, polymorphs, stereoisomers or mixtures thereof. In particular, the present invention relates to a stable immediate release solid oral pharmaceutical composition comprising methacrylic acid copolymer or its derivatives. The invention also provides a process for manufacturing such composition.

BACKGROUND OF THE INVENTION

Tizanidine Hydrochloride is a centrally acting $\alpha_2$ adrenergic agonist and is pharmaceutically used in management of spasticity.

Tizanidine Hydrochloride is chemically known as 5-chloro-4-(2-imidazolin-2-ylamino)-2,1,3-benzothiadiazole monohydrochloride and is represented by the following formula:

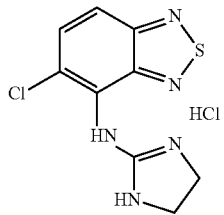 [SMILES: Clc1ccc2nsnc2c1NC1=NCCN1 ; Cl]

Tizanidine Hydrochloride is marketed in the USA as tablets and capsules under the brand names ZANAFLEX®. Inactive ingredients in the ZANAFLEX® capsules include hypromellose, silicon dioxide, sugar spheres, titanium dioxide, gelatin and colorants.

U.S. Pat. No. 3,843,668 discloses Tizanidine and its pharmaceutically acceptable acid addition salts. Example 3 of patent publication discloses preparation of crystals of Tizanidine having melting point of 221-223° C.

U.S. Pat. No. 4,053,617 discloses a method of treating spastic conditions which comprises administering a therapeutically effective amount of Tizanidine or its pharmaceutically acceptable acid addition salts.

U.S. Pat. No. 6,455,557 discloses a method of reducing somnolence in a patient receiving Tizanidine therapy comprising administering to the patient a therapeutically effective amount of Tizanidine in an immediate release multi-particulate pharmaceutical composition with food.

US 2014/0341985 discloses an immediate release multi-particulate Tizanidine oral dosage formulation which comprises a plurality of particles comprising from 2 mg to 12 mg of Tizanidine Hydrochloride and at least one pharmaceutically acceptable excipient. The particles comprise immediate release beads comprising Tizanidine Hydrochloride layered over non-pareil seeds. Tizanidine Hydrochloride immediate release multi-particulates are prepared by spraying a solution of Tizanidine Hydrochloride, hydroxypropyl methylcellulose and silicon dioxide in water over non-pareil seeds (sugar spheres). The disclosed process is an expensive and time consuming process which requires highly specialized equipment and trained personnel. Moreover, control of the manufacturing process is difficult due to various challenges associated with drug layering and control of critical process parameters.

Tizanidine Hydrochloride is approved for oral administration at low doses of 2 to 6 mg. Low doses of Tizanidine Hydrochloride offers manufacturing challenges of ensuring acceptable content uniformity of each of the low dose units. The small amount of drug substance that is typically used for the manufacture of these low dose units must be evenly distributed in a powder blend. Presently marketed capsule formulation of Tizanidine Hydrochloride in the USA (ZANAFLEX®) is a multi-particulate formulation which comprises layering of Tizanidine Hydrochloride over non-pareil seeds. This is an expensive process, requires highly specialized equipment and trained personnel. There exists a need in the pharmaceutical art to develop a simple, reproducible, and cost-effective manufacturing process for preparing stable pharmaceutical compositions of Tizanidine Hydrochloride capsules which offer desired technical attributes such as comparable dissolution and bioequivalence with respect to ZANAFLEX® capsules.

The present inventors developed a simple, reproducible, and cost-effective process for preparing stable pharmaceutical compositions of Tizanidine Hydrochloride. Further, pharmaceutical compositions prepared according to the manufacturing process of the present invention exhibit desired technical attributes such as dissolution and bioequivalence that is comparable to commercially marketed capsule formulation of Tizanidine Hydrochloride.

SUMMARY OF THE INVENTION

One embodiment of the present invention relates to stable pharmaceutical composition comprising Tizanidine or its pharmaceutically acceptable salts, esters, solvates, polymorphs, stereoisomers or mixtures thereof which is bioequivalent to the commercially available counterpart (ZANAFLEX® capsule) after oral administration.

In another embodiment, the present invention provides a process for the preparation of stable pharmaceutical composition of Tizanidine or its pharmaceutically acceptable salts, esters, solvates, polymorphs, stereoisomers or mixtures thereof such that the composition is bioequivalent to the commercially available ZANAFLEX® capsule after oral administration.

Another embodiment of the present invention includes stable solid pharmaceutical composition comprising Tizanidine Hydrochloride which is prepared by direct compression, dry blending, dry granulation or wet granulation process.

Another embodiment of the present invention encompasses a stable pharmaceutical composition comprising Tizanidine Hydrochloride which comprises at least one pharmaceutically acceptable excipient selected from diluent, binder, surfactant, lubricant, glidant and optionally other excipients.

In another embodiment of the present invention, the pharmaceutical composition is substantially free of disintegrant and/or binder.

In another embodiment, the present invention includes a stable pharmaceutical composition comprising Tizanidine Hydrochloride, wherein $D_{90}$ is less than about 200 µm and $D_{50}$ is less than about 80 µm.

Another embodiment of the present invention also provides a process for the preparation of pharmaceutical composition of Tizanidine Hydrochloride, comprising the steps of (a) blending a mixture of Tizanidine Hydrochloride and at least one pharmaceutically acceptable excipient; (b) optionally preparing granules, milling the granules, adding at least one lubricant and optionally other pharmaceutically acceptable excipients to the granules and (c) filling the blend of step (a) or granules of step (b) in capsules.

In another embodiment of the present invention, the granules present in the pharmaceutical composition have bulk density more than or equal to 0.3 g/cm$^3$.

In yet another embodiment of the present invention, the granules present in the pharmaceutical composition have tapped density more than or equal to 0.4 g/cm$^3$.

In another embodiment, at least 30% the granules present in the stable pharmaceutical composition have a diameter of about 850 to about 250 μm [ASTM (American Society for Testing and Materials) standards #20-60 mesh sieve]. Preferably, at least 40% the granules present in the pharmaceutical composition have a diameter of about 850 to about 250 μm [ASTM (American Society for Testing and Materials) standards #20-60 mesh sieve]. More preferably, at least 50% the granules present in the pharmaceutical composition have a diameter of about 850 to about 250 μm [ASTM (American Society for Testing and Materials) standards #20-60 mesh sieve].

In another embodiment, stable pharmaceutical composition of the present invention is placed inside capsule shell of size 00 to 5. Preferably, pharmaceutical composition of the present invention is placed inside capsule shell of size 1 to 4.

In another embodiment, stable pharmaceutical composition of the present invention exhibits a dissolution profile whereby more than 85% of the drug is released within 30 minutes.

In another embodiment, the pharmaceutical composition of the present invention is stable for at least about six months at 40° C. and 75% relative humidity.

In yet another embodiment of the invention, the stable pharmaceutical composition comprises about 0.1 mg to about 40 mg of Tizanidine Hydrochloride.

In further embodiment, the present invention includes a method of using the pharmaceutical composition comprising Tizanidine Hydrochloride in the management of spasticity. In another embodiment of the invention, the stable pharmaceutical composition is suitable for administration once daily or twice daily or three times daily for the management of spasticity.

DETAILED DESCRIPTION OF THE INVENTION

The present invention can be more readily understood by reading the following detailed description of the invention and study of the included examples.

As used herein, the term "composition", as in pharmaceutical composition, is intended to encompass a drug product comprising Tizanidine or its pharmaceutically acceptable salts, esters, solvates, polymorphs, stereoisomers or mixtures thereof, and the other inert ingredient(s) (pharmaceutically acceptable excipients). Such pharmaceutical compositions are synonymous with "formulation" and "dosage form". Pharmaceutical composition of the invention include, but is not limited to, granules, tablets (single layered tablets, multilayered tablets, mini tablets, bioadhesive tablets, caplets, matrix tablets, tablet within a tablet, mucoadhesive tablets, modified release tablets, orally disintegrating tablets, pulsatile release tablets, timed release tablets, delayed release, controlled release, extended release and sustained release tablets), capsules (hard and soft or liquid filled soft gelatin capsules), pills, troches, sachets, powders, microcapsules, minitablets, tablets in capsules and microspheres, matrix composition and the like. Preferably, the pharmaceutical composition refers to tablets and capsules. More preferably, the pharmaceutical composition refers to hard gelatin capsules or HPMC based capsules. Most preferably, the pharmaceutical composition refers to hard gelatin capsules.

The term "excipient" means a pharmacologically inactive component such as a diluent, lubricant, surfactant, carrier, or the like. The excipients that are useful in preparing a pharmaceutical composition are generally safe, non-toxic and are acceptable for veterinary as well as human pharmaceutical use. Reference to an excipient includes both one and more than one such excipient. Co-processed excipients are also covered under the scope of present invention.

The term "bioequivalent" means the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. In practice, two products are considered bioequivalent if the 90% confidence interval of the $C_{max}$, AUC, or, optionally, $T_{max}$ is within the range of 80.00% to 125.00%.

"Substantially free" as used herein refers to the pharmaceutical composition of Tizanidine Hydrochloride, which does not contain binder and/or disintegrant. According to a particularly preferred embodiment, the pharmaceutical composition is substantially free of binder and/or disintegrant. In particular, the pharmaceutical composition comprises less than 1% w/w of binder and/or disintegrant, by total weight of the composition.

Unless otherwise stated the weight percentages expressed herein are based on the final weight of the composition or formulation.

Bulk density, as used herein, refers to the ratio of the mass of an untapped powder sample and its volume including the contribution of the interparticulate void volume. Bulk density indicates mass of a powder material that can be filled in per unit volume. Preferably, granules present in the pharmaceutical composition have bulk density more than or equal to 0.3 g/cm$^3$.

Tapped density, as used herein, refers to the ratio of the mass of a tapped powder sample and its volume. Tapped density of granules is determined using Electrolab tap density tester (Model ETD 1020) where tapping is done at a rate of 500 to 1250 strokes per minute (SPM). Preferably, granules present in the pharmaceutical composition have tapped density more than or equal to 0.4 g/cm$^3$.

The present invention relates to stable pharmaceutical composition of Tizanidine or its pharmaceutically acceptable esters, salts, esters, solvates, polymorphs, stereoisomers or mixtures thereof such that the composition is bioequivalent to the commercially available ZANAFLEX® capsule after oral administration. Preferably, salt of Tizanidine is Tizanidine Hydrochloride.

Tizanidine Hydrochloride in the present invention is used in an amount of about 0.1-50% by weight with respect to total weight of the pharmaceutical composition. Preferably, Tizanidine Hydrochloride in the present invention is used in an amount of about 2-40% by weight with respect to total weight of the pharmaceutical composition.

In another embodiment, the present invention includes particle size of Tizanidine or its pharmaceutically acceptable esters, salts, esters, solvates, polymorphs, stereoisomers or mixtures thereof, wherein $D_{90}$ is less than about 200 μm and $D_{50}$ is less than about 80 μm.

Another embodiment of the present invention includes stable solid pharmaceutical composition comprising Tizanidine Hydrochloride such that the composition is bioequivalent to the commercially available ZANAFLEX® capsule and the composition is prepared by direct compression, dry blending, dry granulation or wet granulation process.

In another embodiment of the invention, the stable pharmaceutical composition comprising Tizanidine Hydrochloride is prepared by using wet or dry granulation process. Any pharmaceutically acceptable granulating solvent or mixture of granulating solvents can be used for wet granulation. Suitable granulating solvents include aqueous or organic solvents. Preferable granulating solvents include, but are not limited to, water, esters such as ethyl acetate; ketones such as acetone; alcohols such as methanol, ethanol, isopropanol, butanol; dichloromethane, chloroform, dimethyl acetamide (DMA), dimethyl sulfoxide (DMSO), ether, diethyl ether and combinations thereof. Preferably, the granulating solvent used during wet granulation is water.

In another embodiment of the invention, wet granulation can be performed using Rapid mixer granulator, Fluid bed granulator, Planetary mixer and the like; dry blending can be performed in V-blender or key blender; and dry granulation can be performed using roller compacter or slugging techniques or by any other method known in the art.

Another embodiment of the present invention encompasses a stable pharmaceutical composition comprising Tizanidine Hydrochloride such that the composition is bioequivalent to the commercially available ZANAFLEX® capsule after oral administration and comprises at least one pharmaceutically acceptable excipient selected from diluent, binder, surfactant, lubricant, glidant and optionally other excipients.

In another embodiment of the invention, the stable pharmaceutical composition is substantially free of disintegrant and/or binder.

Diluents or fillers are substances which usually provide bulk to the composition. Various useful fillers or diluents include, but are not limited to calcium carbonate (Barcroft™, MagGran™, Millicarb™, Pharma-Carb™, Precarb™, Sturcal™, Vivapres Ca™), calcium phosphate, dibasic anhydrous (Emcompress Anhydrous™, Fujicalin™) calcium phosphate, dibasic di hydrate (Calstar™, Di-Cafos™, Emcompress™), calcium phosphate tribasic (Tri-Cafos™, TRI-TAB™), calcium sulphate (Destab™, Drierite™, Snow White™, Cal-Tab™, Compactrol™), cellulose powdered (Arbocel™, Elcema™ Sanacet™), silicified microcrystailine cellulose, cellulose acetate, compressible sugar (Di-Pac™), confectioner's sugar, dextrates (Candex™, Emdex™), dextrin (Avedex™, Caloreen™, Primogran W™), dextrose (Caridex™, Dextrofin™, Tab fine D-IOO™) fructose (Fructofin™, Krystar™), kaolin (Lion™, Sim 90™), lactitol (Finlac DC™, Finlac MCX™), lactose (Anhydrox™, CapsuLac™, Fast-Flo™, FlowLac™, GranuLac™, InhaLac™, Lactochem™, Lactohaïe™, Lactopress™, Microfme™, Microtose™, Pharmatose™, Prisma Lac™, Respitose™, SacheLac™, SorboLac™, Super-Tab™, Tablettose™, Wyndale™, Zeparox™), magnesium carbonate, magnesium oxide (MagGran MO™), maltodextrin (C*Dry MD™, Lycatab DSH™, Maldex™, Maitagran™, Maltrin™, Maltrin QD™, Paselli MD 10 PH™, Star-Dri™), maltose (Advantose 100™), mannitol (Mannogem™, Pearlitol™), microcrystalline cellulose (Avicel PH™, Celex™, Celphere™, Ceolus KG™, Emcocel™, Pharmacel™, Tabulose™, Vivapur™), polydextrose (Litesse™) simethicone (Dow Corning Q7-2243 LVA™, Dow Corning Q7-2587™, Sentry Simethicone™), sodium alginate (Keltone™, Protanal™), sodium chloride (Alberger™) sorbitol (Liponec 70-NC™, Liponic 76-NCv, Meritol™, Neosorb™, Sorbitol Instant™, Sorbogem™), starch (Flufiex W™, Instant Pure-Cote™, Melojel™, Meritena Paygel 55™, Perfectamyl D6PH™, Pure-Cote™, Pure-Dent™, Pure-Gel™, Pure-Set™, Purity 21™, Purity 826™, Tablet White™), pregelatinized starch, sucrose, trehalose and xylitol, or mixtures thereof. Preferably, filler is used in an amount of about 1-90% by weight. More preferably, filler is used in an amount of at least 50% by weight.

Binders impart cohesiveness to formulation. Various useful binders include, but are not limited to acacia, alginic acid (Satialgine H8™), carbomer (Pemulen™, Ultrez™) carboxymethylcellulose sodium (Akucell™, Finnfix™, Tylose™), ceratonia (Meyprofleur™), cottonseed oil, dextrin (Crystal Gum™, Primogran W™), dextrose (Lycedex PF™, Roferose™), gelatin, guar gum (Meprogat™, Meyprodor™, 5 Meyprofm™), hydrogenated vegetable oil type 1 (Sterotex™, Dynasan P[omicron]O™, Softisan 154™, Hydrocote™), hydroxyethyl cellulose (Idroramnosan™, Liporamnosan™, Natrosol™), hydroxyethyhnethyl cellulose (Tylopur MHB™, Tylose MB™, Tyiose MH™, Tylose 10 MHB™), hydroxypropyl cellulose (Klucel™, Methocel™), low substituted hydroxypropyl cellulose, hypromellose (Methocel™, Metolose™, Pharmacoat™, Tylopur™), magnesium aluminium silicate (Magnabite™, Neusilin™, Pharmsorb™ Veegum™), maltodextrin, maltose (Advantose 100™), methylcellulose (Benecel™ Methocel™, Metolose™), microcrystalline cellulose (Avicel PH™, Ceolus KG™, Emcocel™, Ethispheres™, Fibrocel™, Pharmacel™, Tabulose™, Vivapur™), polydextrose (Litesse™), polyethylene oxide (Polyox™), polymethacrylates (Eastacryl 30D™, Eudragit™, Kollicoat MAE 30DP™), povidone (Kollidon™, Plasdone™), sodium alginate (Protanal™), starch (Instant Pure-Cote™, Melojel™, Meritena Paygel 55™, Perfectamyl D6PH™, Pure-Dent™, Pure-Gel™, Pure-Set™, Purity 21™, Purity 826™, Tablet White™), pregelatinised starch, stearic acid, sucrose and zein, or mixtures thereof. Preferably, binder is optionally used in an amount of about 0-10% by weight.

Various useful disintegrants include, but are not limited to, alginic acid (Protacid™, Satialgine H8™), calcium phosphate, tribasic (TRI-TAB™), carboxymethylcellulose calcium (ECG 505™), carboxymethylcellulose sodium (Akucell™, Finnfix™, Nymcel Tylose CB™), colloidal silicon dioxide (Aerosil™, Cab-O-Sil™, Wacker HDK™) croscarmellose sodium (Ac-Di-Sol™, Pharmacel XL™, Primellose™, Solutab™, Vivasol™), crospovidone (Kollidon CL™, Kollidon CL-M™, Polyplasdone XL™) docusate sodium, guar gum (Meyprodor™, Meyprofin™, Meyproguar™), low substituted hydroxypropyl cellulose, magnesium aluminum silicate (Magnabite™, Neusilin™, Pharmsorb™, Veegum™), methylcellulose (Methocel™, Metolose™), microcrystalline cellulose (Avicel PH™, Ceolus KG™, Emcoel™, Ethispheres™, Fibrocel™, Pharmacel™, Vivapur™), povidone (Kollidon™, Plasdone™) sodium alginate (Kelcosol™, Ketone™, Protanal™), sodium starch glycolate, polacrilin potassium (Amberlite IRP88™), silicified microcrystalline cellulose (ProSotv™), starch (Aytex P™, Fluftex W™, Melojel™, Meritena™, Paygel 55™, Perfectamyl D6PH™, Pure-Bind™, Pure-Cote™, Pure-Dent™, Purity 21™, Purity 826™, Tablet White™) or pre-gelatinized starch (Lycatab PGS™, Merigel™, National 78-1551™, Pharma-Gel™, Prejel™, Sepistab ST 200™, Spress B82O™, Starch 1500 G™, Tablitz™, Unipure LD™), or mixtures thereof. Preferably, disintegrant is optionally used in an amount of about 0-10% by weight.

Lubricants are added to a pharmaceutical composition for ease in processing, to prevent adhesion to the equipment during processing. Lubricants used in the composition include, but are not limited to, calcium stearate (HyQual™), glycerine monostearate (Imwitor™ 191 and 900, Kessco GMS5™, 450 and 600, Myvaplex 600P™, Myvatex™, Rita GMS™, Stepan GMS™, Tegin™, Tegin™ 503 and 515, Tegin 4100™, Tegin M™, Unimate GMS™), glyceryl behenate (Compritol 888 ATO™), glyceryl palmitostearate (Precirol ATO 5™), hydrogenated castor oil (Castorwax MP 80™, Croduret™, Cutina HR™, Fancol™, Simulsol 1293™), hydrogenated vegetable oil 0 type I (Sterotex™, Dynasan P60™, Hydrocote™, Lipovol HS-K™, Sterotex HM™), magnesium lauryl sulphate, magnesium stearate, medium-chain triglycerides (Captex 300™, Labrafac CC™, Miglyol 810™, Neobee M5™, Nesatol™, Waglinol 3/9280™), poloxamer (Pluronic™, Synperonic™), polyethylene 5 glycol (Carbowax Sentry™, Lipo™, Lipoxol™, Lutrol E™, Pluriol E™), sodium benzoate (Antimol™), sodium chloride, sodium lauryl sulphate (Elfan 240™, Texapon Kl 2P™), sodium stearyl fumarate (Pruv™), stearic acid (Hystrene™, industrene™, Kortacid 1895™, Pristerene™), talc (Altaic™, Luzenac™, Luzenac Pharma™, Magsil Osmanthus™, 0 Magsil Star™, Superiore™), sucrose stearate (Surfhope SE Pharma D-1803 F™) and zinc stearate (HyQual™) or mixtures thereof. Preferably, lubricant is present in an amount of about 0.1-5% by weight.

Glidants improve flowability and accuracy of dosing. Glidants used in the composition include, but are not limited to, tribasic calcium phosphate (TRI-TAB™), calcium silicate, cellulose, powdered (Sanacel™, Solka-Floc™), colloidal silicon dioxide (Aerosil™, Cab-O-Sil M-5P™, Wacker HDK™), magnesium silicate, magnesium trisilicate, starch (Melojel™, Meritena™, Paygel 55™, Perfectamyl D6PH™, Pure-Bind™, Pure-Cote™, Pure-Dent™, Pure-Gel™, Pure-Set™, Purity 21™, Purity 826™, Tablet White™) and talc (Luzenac Pharma™, Magsil Osmanthus™, Magsil Star™, Superiore™) or mixtures thereof. Preferably, the glidant is used in an amount of about 0.1-15% by weight.

Pharmaceutically acceptable surfactants include, but are limited to both non-ionic and ionic surfactants suitable for use in pharmaceutical dosage forms. Ionic surfactants may include one or more of anionic, cationic or zwitterionic surfactants. Examples include, but are not limited to, sodium lauryl sulfate, monooleate, monolaurate, monopalmitate, monostearate or another ester of olyoxyethylene sorbitane, sodium dioctylsulfosuccinate (DOSS), lecithin, stearyic alcohol, cetostearylic alcohol, cholesterol, polyoxyethylene ricin oil, polyoxyethylene fatty acid glycerides, poloxamer, or any other commercially available co-processed surfactant like SEPITRAP® 80 or SEPITRAP® 4000 and mixtures thereof. Preferably, the surfactant is used in an amount of about 0-5% by weight.

In another embodiment of the invention, polymers suitable for use in the present invention include pH dependent as well as pH independent polymers.

In another embodiment of the invention, pH dependent polymers suitable for use in the present invention include, but are not limited to, cellulose acetate phthalate (CAP), cellulose acetate trimellitate (CAT), hydroxypropylmethylcellulose phthalate (HPMCP), hydroxypropylmethylcellulose acetate succinate (HPMCAS), hydroxypropylcellulose acetate phthalate (HPCAP), hydroxypropylmethylcellulose acetate phthalate (HPMCAP), methylcellulose acetate phthalate (MCAP) and methacrylic acid copolymers or its derivatives. Methacrylic acid copolymers or its derivatives are available under various trade names such as EUDRAGIT®, Acryl-EZE®, Eastacryl®, and Kollicoat® from Evonik Industries, Colorcon, Eastman Chemical and BASF Fine Chemicals respectively. Preferred pH dependent methacrylic acid copolymers or its derivatives suitable for use in the present invention include anionic copolymers such as, but not limited to, Eudragit® L 100-55, Acryl-EZE, Eudragit® L 30 D-55, PlasACRYL™ HTP20, Eudragit® L 100, Eudragit® L 12.5, Eudragit® S 100, Eudragit® S 12.5, Eudragit® FS 30 D, PlasACRYL™ T20 etc. More preferably, suitable anionic methacrylic acid copolymers or its derivative include Eudragit® L 100-55, Acryl-EZE and Eudragit® L 30 D-55. Preferably, the pH dependent polymer is used in an amount of about 0.1-45% by weight.

In another embodiment of the invention, pH independent polymers suitable for use in the present invention include, but are not limited to, alkylcelluloses, such as methylcellulose, ethylcellulose; hydroxyalkylcelluloses, for example, hydroxymethyl cellulose, hydroxyethyl cellulose, hydroxypropyl cellulose and hydroxybutylcellulose; hydroxyalkyl alkylcelluloses, such as hydroxyethyl methylcellulose and hydroxypropyl methylcellulose (hypromellose); carboxyalkylcelluloses, such as carboxymethylcellulose; alkali metal salts of carboxyalkylcelluloses, such as sodium carboxymethylcellulose; carboxyalkyl alkylcelluloses, such as carboxymethyl ethylcellulose; carboxyalkylcellulose esters; other natural, semi-synthetic, or synthetic polysaccharides, such as alginic acid, alkali metal and ammonium salts thereof, carrageenans, galactomannans, tragacanth, agar-agar, gum arabic, guar gum, xanthan gum, starches, pectins, such as sodium carboxymethyl amylopectin, chitin derivates, such as chitosan, polyfructans, inulin; polyacrylic acids and the salts thereof; polymethacrylic acids, and the salts thereof, methacrylate copolymers; polyvinylalcohol; polyvinylpyrrolidone (povidone), copolymers of polyvinylpyrrolidone with vinyl acetate; combinations of polyvinylalcohol and polyvinylpyrrolidone; polyalkylene oxides, such as polyethylene oxide and polypropylene oxide and copolymers of ethylene oxide and propylene oxide; and combinations thereof. Methacrylic acid copolymers or its derivative suitable for use in the present invention include, but are not limited to, Eudragit® RL PO, Eudragit® RL 100, Eudragit® RL 30 D, Eudragit® RL 12.5, Eudragit® RS PO, Eudragit® RS 100, Eudragit® RS 30 D, Eudragit® RS 12.5, Eudragit® NE 30 D, Eudragit® NE 40 D, Eudragit® NM 30 D etc. Preferably, the pH independent polymer is used in an amount of about 0.1-45% by weight.

In another embodiment of the invention, the pharmaceutical composition is formulated into solid oral pharmaceutical dosage forms. Solid oral pharmaceutical dosage forms include, but are not limited to, tablets, capsules, powders, granules and sachets. Preferably, the solid oral pharmaceutical dosage form is a tablet or capsule. More preferably, the solid oral pharmaceutical dosage form is a capsule.

In yet another embodiment of the invention, the pharmaceutical composition comprises about 0.1 mg to about 40 mg of Tizanidine Hydrochloride. Preferably, the pharmaceutical composition comprises about 2 mg to about 18 mg of Tizanidine Hydrochloride. More preferably, the pharmaceutical composition comprises about 2 mg to about 6 mg of Tizanidine Hydrochloride.

In another embodiment, at least 30% of the granules present in the pharmaceutical composition have a diameter of about 850 to about 250 μm [ASTM (American Society for Testing and Materials) standards #20-60 mesh sieve]. Preferably, at least 40% the granules present in the pharmaceutical composition have a diameter of about 850 to about 250 µm [ASTM (American Society for Testing and Materials) standards #20-60 mesh sieve]. More preferably, at least 50% the granules present in the pharmaceutical composition have a diameter of about 850 to about 250 µm [ASTM (American Society for Testing and Materials) standards #20-60 mesh sieve].

Diameter of granules is determined using Retsch AS 200 magnetic sieve shaker at an amplitude of 30 to 90 Hz with time interval between 5 to 30 minutes (Refer: USP 29 <786> Particle size distribution estimation by analytical sieving).

In another embodiment, pharmaceutical composition of the present invention is placed inside capsule shell of size 1 to 4.

The capsule dosage form prepared by the above process can be subjected to in vitro dissolution evaluation according to Test 711 "Dissolution" in the United States Pharmacopoeia 37, United States Pharmacopoeial Convention, Inc., Rockville, Md., 2014 ("USP") to determine the rate at which the active substance is released from the dosage form, and the content of the active substance can be determined in solution by high performance liquid chromatography. When comparing the test and reference products, dissolution profiles should be compared using a similarity factor ($f_2$). The similarity factor is a logarithmic reciprocal square root transformation of the sum of squared error and is a measurement of the similarity in the percent (%) of dissolution between the two curves.

$$f_2 = 50 \log \{[1+(1/n)\Sigma_{t=1}^{n}(R_t-T_t)^2]^{-0.5} \cdot 100\}$$

Two dissolution profiles are considered similar when the $f_2$ value is equal to or greater than 50.

In another embodiment, pharmaceutical composition of the present invention exhibits more than 85% of drug release within 30 minutes in 500 ml of 0.01 N HCl (Office of Generic Drugs dissolution database) using a USP II apparatus (paddle) at a temperature of 37±0.5° C. and a rotation speed of 50 revolutions per minute.

Another embodiment of the present invention also provides a process for the preparation of pharmaceutical composition of Tizanidine Hydrochloride, comprising the steps of (a) blending a mixture of Tizanidine Hydrochloride and at least one pharmaceutically acceptable excipient, (b) optionally preparing granules, milling the granules, adding at least one lubricant and optionally other pharmaceutically acceptable excipients to the granules and (e) filling the blend of step (a) or granules of step (b) in capsules.

The process of the present invention besides being cost effective, also makes it possible to prepare a pharmaceutical composition of Tizanidine Hydrochloride, wherein the composition has desirable technical attributes such as comparable dissolution and bioequivalence with respect to ZANAFLEX® capsules.

In another embodiment, pharmaceutical composition of the present invention particularly capsule dosage form of present invention can be packaged in HDPE bottles or blister packs. HDPE bottles may optionally contain desiccants.

Another embodiment of the present invention includes method of using the pharmaceutical composition comprising Tizanidine Hydrochloride in the management of spasticity.

As used herein, the term "about" means±approximately 20% of the indicated value, such that "about 10 percent" indicates approximately 08 to 12 percent.

Having described the invention with reference to certain preferred embodiments, other embodiments will become apparent to one skilled in the art from consideration of the specification. The invention is further defined by reference to the following examples describing in detail method for the preparation and testing of Tizanidine Hydrochloride pharmaceutical composition. It will be apparent to those skilled in the art that many modifications, both to materials and methods, may be practiced without departing from the scope of the invention. Following examples are set out to illustrate the invention and do not limit the scope of the present invention.

EXAMPLES

Example I

Tizanidine Hydrochloride capsule dosage form was prepared by dry granulation process by using formula as given in Table 1:

TABLE 1

| Ingredient | Functional category | Quantity (% w/w) |
|---|---|---|
| Tizanidine Hydrochloride | Active Ingredient | 3.00 |
| Lactose | Diluent | 70.00 |
| Stearic acid | Lubricant | 4.00 |
| Methacrylic Acid - Ethyl Acrylate Copolymer | Polymer | 23.00 |

The processing steps involved in the manufacturing of capsule dosage form is given below:
  i) Tizanidine Hydrochloride, Lactose, Stearic acid and Methacrylic acid copolymer were sifted through a suitable sieve.
  ii) The sifted blend of step i) was compacted to prepare slugs.
  iii) Slugs obtained in step ii) were milled to prepare granules.
  iv) The granules obtained in step iii) were screened using suitable sieve.
  v) Granules obtained from step iv) were lubricated with Stearic acid and filled into hard gelatin capsules.

Example II

Tizanidine Hydrochloride capsule dosage form was prepared by dry granulation process by using formula as given in Table 2:

TABLE 2

| Ingredient | Functional category | Quantity (% w/w) |
|---|---|---|
| Tizanidine Hydrochloride | Active | 3.00 |
| Mannitol | Diluent | 75.00 |
| Magnesium stearate | Lubricant | 3.00 |
| Methacrylic Acid - Ethyl Acrylate Copolymer | Polymer | 19.00 |

The processing steps involved in the manufacturing of capsule dosage form is given below:
  i) Tizanidine Hydrochloride, Mannitol, Magnesium stearate and Methacrylic acid copolymer were sifted through a suitable sieve.
  ii) The sifted blend of step i) was compacted to prepare slugs.
  iii) Slugs obtained in step ii) were milled to prepare granules.

iv) The granules obtained in step iii) were screened using suitable sieve.

v) Granules obtained from step iv) were lubricated with Magnesium stearate and filled into hard gelatin capsules.

Example III

The standardized method and equipment for testing dissolution time is provided in Office of Generic Drugs dissolution database. The dissolution profile of capsule dosage form prepared using quantitative composition as given in Table 1 was measured in 500 ml of 0.01 N HCl (Office of Generic Drugs dissolution database) using a USP II apparatus (paddle) at a temperature of 37±0.5° C. and a rotation speed of 50 revolutions per minute. The dissolution test was conducted on the reference formulation ZANAFLEX® capsules in comparison to a capsule dosage form as given in Example 1. The dissolution data is provided in Table 3.

TABLE 3

| Time point | % drug released | |
|---|---|---|
| (min.) | Reference | Example I |
| 5 | 75 | 71 |
| 10 | 95 | 95 |
| 15 | 97 | 97 |
| 20 | 98 | 97 |
| 30 | 97 | 97 |
| f2 value | — | 84 |

Since, both commercially available ZANAFLEX® capsules and capsule dosage form prepared using quantitative composition as given in Table 1 exhibited more than 85% of drug release within 15 minutes, dissolution profiles of the two formulations were found to be similar and similarity factor (f2) was found to be more than 50.

Example IV

Capsule dosage form prepared in Example I was subjected to Accelerated stability testing as per the ICH guidelines at temperature/relative humidity of 40°±2° C./75%±5% RH for 6 months. The capsule dosage form was placed in a high density polyethylene (HDPE) bottle with induction sealing and analyzed for drug content by High Performance Liquid Chromatography (HPLC) method. The prepared dosage form was found to be stable and exhibited following assay values (in the Table 4):

TABLE 4

| Study period | Acceptable limits | Amount of Tizanidine Hydrochloride in the Capsule dosage form Example I |
|---|---|---|
| Initial | 90%-110% | 98.5% |
| After six months | 90%-110% | 95.0% |

Example V

A bioequivalence study comparing the capsule dosage forms prepared in Example I (Test product, T) with commercially available Reference product ZANAFLEX® capsules (Reference product, R) was performed in forty nine healthy adult human subjects and plasma drug concentrations were determined at regular intervals after dosing. The following parameters were calculated for test and reference product:

$AUC_{0-t}$=Area under plasma drug concentration versus time curve, from time zero (drug administration) to the last measurable concentration.

$AUC_{0-inf}$=Area under the plasma drug concentration versus time curve, from time zero to infinity.

$T_{max}$=Time after dosing until the maximum measured plasma drug concentration.

$C_{max}$=Maximum plasma drug concentration.

T/R (Test vs Reference) ratio was determined for the calculated pharmacokinetic parameters and is tabulated in Table 5.

TABLE 5

| Pharmacokinetic parameter | T/R Ratio (%) |
|---|---|
| $C_{max}$ | 96.63 |
| $AUC_{0-t}$ | 104.61 |
| $AUC_{0-inf}$ | 104.47 |

T/R ratio for AUC of about 100% indicates that the capsule dosage form prepared in Example I shows similar mean pharmacokinetic parameters when compared against commercially available reference product ZANAFLEX® capsules which establishes that the capsule dosage form prepared in Example I was bioequivalent to the commercially available Reference product ZANAFLEX® capsules.

Many modifications of this invention can be made without departing from its spirit and scope, as will be evident to those skilled in the art. The specific embodiments described herein are provided by way of example only, and the invention is to be limited only by the terms of the appended claims, along with the full scope of equivalents to which such claims are entitled.

We claim:

1. A stable immediate release solid oral pharmaceutical dosage form comprising tizanidine or its pharmaceutically acceptable salts, wherein:
   a) the dosage form comprises granules comprising a mixture of said tizanidine and one or more anionic pH dependent methacrylic acid copolymers; and
   b) not less than 80% by weight of the tizanidine is released within 30 minutes after said dosage form is placed in a dissolution vessel filled with 500 ml of 0.01 N hydrochloric acid maintained at 37.0±5° C. and stirred at a paddle speed of 50 rpm using a USP Type II (paddle) apparatus;

wherein the dosage form is stable for at least six months at 40° C. at 75% relative humidity.

2. A stable immediate release pharmaceutical capsule dosage form comprising tizanidine or its pharmaceutically acceptable salts, wherein:
   a) the dosage form comprises granules comprising a mixture of said tizanidine and one or more anionic pH dependent methacrylic acid copolymers;
   b) the dosage form is substantially free of binder and/or disintegrant; and
   c) not less than 80% by weight of said tizanidine is released within 30 minutes after said dosage form is placed in a dissolution vessel filled with 500 ml of 0.01 N hydrochloric acid maintained at 37.0±5° C. and stirred at a paddle speed of 50 rpm using a USP Type II (paddle) apparatus.

3. The stable immediate release solid oral pharmaceutical dosage form of claim 1, wherein the dosage form is a tablet or a capsule.

4. The stable immediate release pharmaceutical capsule dosage form of claim 3, wherein the dosage form is bioequivalent to the marketed form of tizanidine marketed under the brand name ZANAFLEX® capsule after oral administration.

5. The stable pharmaceutical dosage form of claim 1, wherein the dosage form is prepared by dry blending or direct compression or granulation process.

6. The stable pharmaceutical dosage form of claim 1, wherein the dosage form further comprises a pharmaceutically acceptable excipient selected from at least one of diluent, surfactant, lubricant, glidant, or pH independent polymers.

7. The stable pharmaceutical dosage form of claim 1, wherein the methacrylic acid copolymer comprises a methacrylic acid-ethyl acrylate copolymer.

8. The stable pharmaceutical dosage form of claim 1, wherein the pharmaceutically acceptable salt comprises tizanidine hydrochloride.

9. The stable pharmaceutical dosage form of claim 1, wherein tizanidine or its pharmaceutically acceptable salts is present in an amount ranging from about 0.1 mg to about 40 mg.

10. A process for preparation of an immediate release pharmaceutical capsule dosage form comprising tizanidine hydrochloride, wherein the composition comprises one or more anionic pH dependent methacrylic acid copolymers, the process comprising:
(a) blending a mixture of tizanidine hydrochloride, the one or more anionic pH dependent methacrylic acid copolymers, and at least one pharmaceutically acceptable excipient;
(b) optionally preparing granules, milling the granules, adding at least one lubricant and optionally other pharmaceutically acceptable excipients to the granules; and
(c) filling the blend of step (a) or granules of step (b) in capsules, wherein
not less than 80% by weight of the tizanidine hydrochloride is released within 30 minutes after said capsule dosage form is placed in a dissolution vessel filled with 500 ml of 0.01 N hydrochloric acid maintained at 37.0±5° C. and stirred at a paddle speed of 50 rpm using a USP Type II (paddle) apparatus.

11. The immediate release pharmaceutical capsule dosage form of claim 3, wherein the dosage form is free of binder and/or disintegrant.

12. The immediate release pharmaceutical capsule dosage form of claim 3, wherein the dosage form comprises tizanidine hydrochloride, about 70% (w/w) lactose, about 4% (w/w) stearic acid and about 23% (w/w) methacrylic acid-ethyl acrylate copolymer.

13. The immediate release pharmaceutical capsule dosage form of claim 3, wherein the dosage form comprises tizanidine hydrochloride, about 75% (w/w) mannitol, about 3% (w/w) magnesium stearate and about 19% (w/w) methacrylic acid-ethyl acrylate copolymer.

14. The immediate release pharmaceutical capsule dosage form of claim 3, wherein the dosage form comprises between about 2-40% (w/w) of tizanidine hydrochloride.

15. The immediate release pharmaceutical capsule dosage form of claim 3, wherein the dosage form comprises about 3% (w/w) of tizanidine hydrochloride.

16. The immediate release pharmaceutical capsule dosage form of claim 3, wherein the dosage form comprises tizanidine hydrochloride having a D90 particle size less than about 200 microns and a D50 less than about 80 microns.

17. The immediate release pharmaceutical capsule dosage form of claim 3, wherein the dosage form comprises about 0.1-45% (w/w) of pH dependent methacrylic acid copolymers or their derivatives.

18. The immediate release pharmaceutical capsule dosage form of claim 3, wherein the dosage form comprises about 3% (w/w) of pH dependent methacrylic acid copolymers.

19. The immediate release pharmaceutical dosage form of claim 1, wherein the composition includes tizanidine HCl as the sole active ingredient in the dosage form.

20. The stable pharmaceutical dosage form of claim 2, wherein the pharmaceutically acceptable salt comprises tizanidine hydrochloride.

* * * * *